(12) United States Patent
Benz et al.

(10) Patent No.: US 11,819,980 B2
(45) Date of Patent: Nov. 21, 2023

(54) MANDREL FOR HOLDING A LENS BLANK AND METHOD OF MAKING A LENS USING THE SAME

(71) Applicants: Benz Research and Development Corp., Sarasota, FL (US); Patrick H. Benz, Santa Barbara, CA (US); Andrew A. Larson, Blaine, MN (US)

(72) Inventors: Patrick H. Benz, Santa Barbara, CA (US); Andrew A. Larson, Blaine, MN (US)

(73) Assignee: Benz Research and Development Corp., Sarasota, FL (US)

(*) Notice: Subject to any disclaimer, the term of this patent is extended or adjusted under 35 U.S.C. 154(b) by 257 days.

(21) Appl. No.: 17/119,607

(22) Filed: Dec. 11, 2020

(65) Prior Publication Data

US 2021/0178555 A1 Jun. 17, 2021

Related U.S. Application Data

(60) Provisional application No. 62/947,339, filed on Dec. 12, 2019.

(51) Int. Cl.
*B25B 11/00* (2006.01)
*A61F 2/16* (2006.01)
(Continued)

(52) U.S. Cl.
CPC ............... *B25B 11/00* (2013.01); *A61F 2/16* (2013.01); *B23Q 3/086* (2013.01);
(Continued)

(58) Field of Classification Search
CPC .............. B24B 13/0006; B24B 13/005; B24B 13/0055; B29D 11/00942; B29D 11/023;
(Continued)

(56) References Cited

U.S. PATENT DOCUMENTS

| | | |
|---|---|---|
| 3,951,203 A | 4/1976 | Prunier |
| 4,856,234 A | 8/1989 | Goins |

(Continued)

FOREIGN PATENT DOCUMENTS

| | | | |
|---|---|---|---|
| EP | 2 988 925 A1 | 3/2016 | |
| WO | WO-2014/176230 A1 | 10/2014 | |
| WO | WO-2019020420 A1 * | 1/2019 | ............. B23B 31/34 |

OTHER PUBLICATIONS

Translation of WO-2019020420-A1 (Year: 2019).*

(Continued)

*Primary Examiner* — Matthew P Travers
(74) *Attorney, Agent, or Firm* — FOLEY & LARDNER LLP

(57) ABSTRACT

A mandrel for holding and positioning an intraocular lens blank during manufacturing includes a shank portion having a central axis and a lens blank holding section configured to hold the lens blank. The holding section includes a central cavity formed concentrically with the central axis of the mandrel. Projections are formed on a surface of the central cavity and are configured to support a first surface of the lens blank at a fixed distance from the surface of the central cavity. A ring fits within a peripheral portion of the central cavity to hold a second opposing surface of the lens blank. A method for making an intraocular lens using the mandrel includes filling the space formed under the first surface of the lens with a liquid, such as water, freezing the liquid, and then machining and/or milling the second surface of the lens blank.

12 Claims, 10 Drawing Sheets

(51) Int. Cl.
*B24B 13/005* (2006.01)
*B29D 11/00* (2006.01)
*B23Q 3/08* (2006.01)
*B29D 11/02* (2006.01)
*B29L 11/00* (2006.01)

(52) U.S. Cl.
CPC .... *B24B 13/0055* (2013.01); *B29D 11/00942* (2013.01); *A61F 2240/001* (2013.01); *B29D 11/023* (2013.01); *B29L 2011/0016* (2013.01)

(58) Field of Classification Search
CPC ....... B25B 11/00; B25B 11/005; B23Q 3/086; A61F 2240/001; A61F 2/16; A61F 2002/1681; B29L 2011/0016; B29L 2031/7532
See application file for complete search history.

(56) References Cited

U.S. PATENT DOCUMENTS

| | | | |
|---|---|---|---|
| 5,080,482 A * | 1/1992 | Benz | B23Q 17/24 356/127 |
| 9,919,487 B2 | 3/2018 | Benz et al. | |
| 2004/0002290 A1 | 1/2004 | Green | |
| 2011/0037184 A1 | 2/2011 | Shoji et al. | |
| 2011/0124272 A1 | 5/2011 | Felten et al. | |
| 2014/0277437 A1* | 9/2014 | Currie | A61F 2/1624 623/6.37 |

OTHER PUBLICATIONS

International Search Report and Written Opinion dated Aug. 21, 2014 in PCT/US2014/034935 (10 pgs.).
International Preliminary Report on Patentability on PCT/US2020/064554 dated Jun. 23, 2022 (8 pages).
International Search Report and Written Opinion for International Application No. PCT/US2020/064554 dated Mar. 29, 2021, 9 pages.

* cited by examiner

MANDREL FOR HOLDING A LENS BLANK AND METHOD OF MAKING A LENS USING THE SAME

CROSS-REFERENCE TO RELATED PATENT APPLICATIONS

This application claims priority from Provisional Application U.S. Application 62/947,339, filed Dec. 12, 2019, incorporated herein by reference in its entirety.

FIELD

This invention relates to a mandrel for holding a lens, such as an intraocular lens, and a method of making a lens, more specifically, a method of making a one-piece lens, such as an intraocular lens using the mandrel.

BACKGROUND

As set forth in commonly assigned U.S. Pat. No. 9,919,487 (the "'487 patent", which is hereby incorporated by reference for all purposes), intraocular lenses are typically produced by machining and milling a polymer disc (i.e., a lens "blank") that is held in place typically by wax or water (ice) during the fabrication process. Wax, either water soluble wax or solvent soluble wax, is used for fabricating hydrophilic intraocular lenses and ice is used when cryogenically fabricating hydrophobic intraocular lenses, which are rubbers at room temperature and require low temperatures for machining. Each side of the polymer blank is machined and milled in turn, with the final product being a completed single piece intraocular lens. Specifically, milling is performed on a first side of the disc by holding the disc on a first-side mandrel. The partially machined blank is then held on a second-side mandrel so that the second side of the blank may be milled.

The '487 patent discloses an improved mandrel that is particularly beneficial when used as a second-side mandrel for holding a partially machined and/or molded hydrophilic lens blank with blocking wax. In contrast, lenses made of hydrophobic materials typically are formed cryogenically, which presents particular challenges in terms of ensuring that the optic and the haptic are centered.

SUMMARY

In one exemplary embodiment, a mandrel for holding and positioning an intraocular lens blank during manufacturing includes a shank portion having a central axis and a lens blank holding section to hold the lens blank. The holding section includes a central cavity formed concentrically with the central axis of the mandrel. Projections are formed on the surface of the central cavity to support a first surface of the lens blank. A ring fits within the periphery of the lens blank holding section, and holds a second opposing surface of the lens blank.

In one exemplary embodiment, a space is formed between the first surface of a lens blank as the lens blank is supported by the projections and the surface of the central cavity.

In one exemplary embodiment, a hollow channel is formed within the central cavity, the hollow channel extending into the shank.

In one exemplary embodiment, the shank portion is configured to be received within a supporting collet.

In one exemplary embodiment, a second cavity is concentric with the central cavity and has a smaller cross-sectional diameter than the central cavity.

In one exemplary embodiment, an interference fit retains the ring portion within the lens holding section.

In one exemplary embodiment, the ring portion includes a plurality of holes formed along an inner peripheral surface thereof, the holes being configured to permit a liquid, preferably water, to be transferred into the space formed between the first surface of a lens blank as the lens blank is supported by the projections and the surface of the central cavity. The water may be frozen to support the lens blank as it is milled and/or machined.

According to one exemplary embodiment, a method for making an intraocular lens using the mandrel includes providing a mandrel, positioning an intraocular lens blank in the central cavity of the mandrel, and fitting the ring to the mandrel so as to hold the intraocular lens blank on the mandrel.

According to one exemplary embodiment, the optical center of the intraocular lens blank is positioned concentrically with the central axis of the mandrel shank.

According to one exemplary embodiment, the method further includes applying a liquid to a space formed between the first surface of a lens blank as the lens blank is supported by the projections and the surface of the central cavity, freezing the liquid so that it supports the lens blank, and forming a lens from the lens blank.

According to one exemplary embodiment, forming the lens comprises one or more of milling or machining a second surface of the lens as it is supported within the mandrel.

According to one exemplary embodiment, the liquid preferably comprises water and the lens blank preferably comprises a hydrophobic material.

According to one exemplary embodiment, the mandrel is held in a vacuum collet and the lens is formed with a laser.

BRIEF DESCRIPTION OF THE DRAWINGS

The accompanying drawings, which are incorporated in and constitute a part of this specification, illustrate embodiments of the invention and together with the description serve to explain principles of the invention.

DETAILED DESCRIPTION OF THE PREFERRED EMBODIMENTS

Conventional techniques for machining a lens blank on a mandrel present several challenges. For example, it is critical to ensure that the blank is held in proper alignment, particularly when milling the second side surface so that the haptic of the blank is properly centered. With conventional techniques, it is difficult to ensure accuracy, especially with hydrophobic lens materials that are milled cryogenically.

Figure 1:
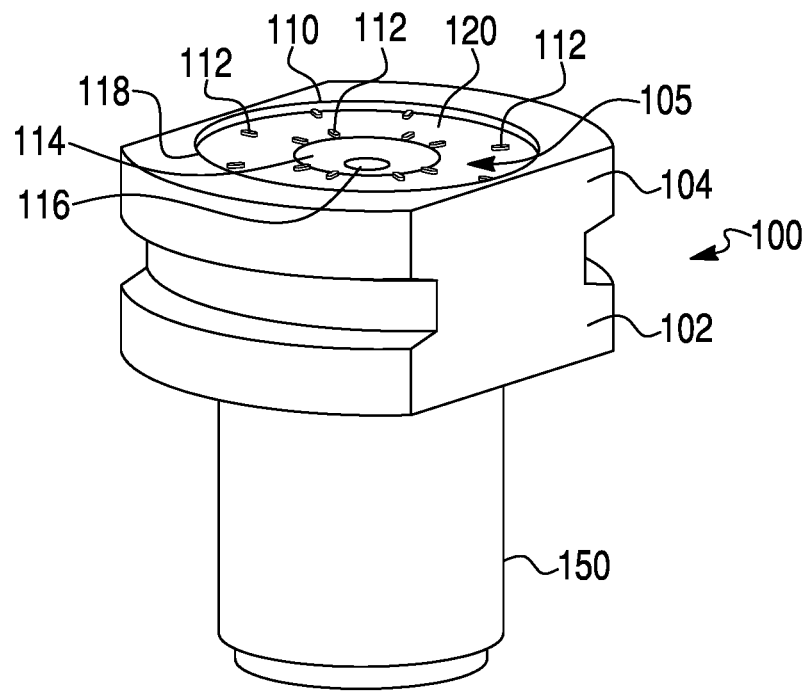
FIG. 1 shows a perspective view of a mandrel according to one embodiment.

FIG. 1 depicts a mandrel 100 according to one embodiment. The mandrel 100 is configured for holding a lens blank during manufacturing. Preferably, the mandrel 100 is a second-side mandrel, meaning that the mandrel 100 is a mandrel to which a lens blank is transferred to from a first-side collet or a first-side mandrel, after a first side of the lens blank is partially machined. The second side of the lens blank may then be machined on the second-side mandrel. The mandrel 100 may be fabricated from, for example, a polymer, preferably, a glassy polymer material.

The mandrel 100 includes a hollow mandrel shank 150 that is configured to fit precisely within a collet during milling of a lens blank. The mandrel 100 may be formed, for example, by injection molding. Preferably, the mandrel 100 is formed with precise dimensions to maintain a precise height of a lens blank to be milled when the mandrel 100 is received in a collet, as discussed further below. Preferably, the diameter of the mandrel shank 150 is precisely controlled (for example, ±≤0.01 mm), as is the roundness of the mandrel shank 150 (for example, ±≤0.01 mm TIR).

According to an exemplary embodiment, the top or head portion 102 of the mandrel 100 has one or more substantially planar side surfaces 104. These side surfaces 104 may be used advantageously to locate the meridian of haptics (M) to be formed from a lens blank. In certain non-limiting embodiments, information pertaining to the lens blank may be positioned on the side surfaces 104. For example, a bar code (not shown) may be applied to one or both substantially planar side surfaces 104 of the mandrel 100 containing identifying information, such as part number, optical power, type of material used, testing and/or quality control information.

The mandrel 100 includes a lens blank holding section 105 configured to hold a lens blank. In this embodiment, the lens blank holding section 105 includes a central cavity 110 having a sidewall 118 and a bottom surface 120. The sidewall 118, in this embodiment, is substantially parallel to the central axis (X) of the mandrel 100. Formed on the bottom surface 120 of the lens blank holding section 105 of the mandrel 100, within the central cavity 110, are a plurality of projections 112. The plurality of projections 112 are configured to support a lens blank at a predetermined distance above the bottom surface 120 of the central cavity 110. In this embodiment, the plurality of projections 112 are disposed radially from the central axis (X) of the mandrel 100. Preferably, the plurality of projections 112 are positioned at locations such that they do not interfere with the milling of a lens blank to form the haptics of an intraocular lens.

In this embodiment, the lens blank holding section 105 further includes a second cavity 114. The second cavity 114 is formed within the central cavity 110. The second cavity 114 is concentric with the central cavity 110 and the central axis (X) of the mandrel 100. The second cavity 114 has a smaller cross-sectional diameter than the central cavity 110. A hollow center channel 116 is formed within the second cavity 114. The hollow center channel 116 is configured to provide an outlet through which air, liquid, and/or a frozen liquid may pass through as discussed further below. The central cavity 110 may be rounded, may have a conical shape, or may have a truncated conical shape. Additionally, the second cavity 114 may be rounded, may have a conical shape, or may have a truncated conical shape.

Figure 2:
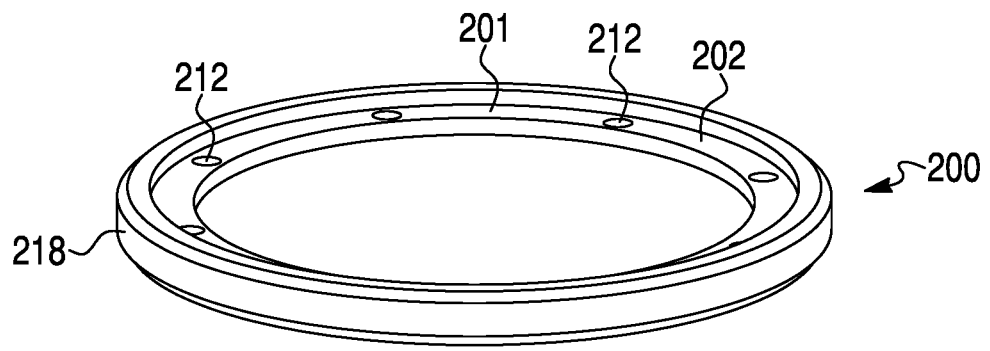
FIG. 2 shows a perspective view of an embodiment of a ring for use with the mandrel according to FIG. 1.
Figure 3:
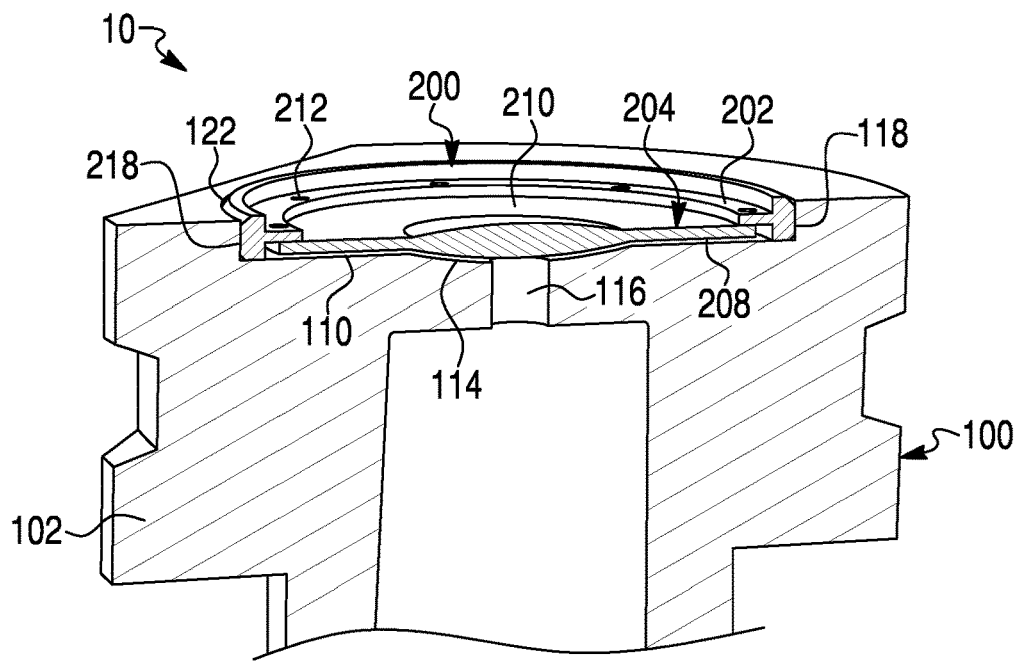
FIG. 3 shows a cross-sectional view of a mandrel/optic disc assembly including the mandrel according to FIG. 1 with the ring according to FIG. 2 holding a lens blank onto the mandrel.

FIG. 2 shows an embodiment of a ring 200 configured to be received within a periphery of the central cavity 110 of the lens blank holding section 105 of the mandrel 100. In this embodiment, the ring 200 has a sidewall 218 that is configured to fit against the sidewall 118 of the central cavity 110 to form an interference fit between the ring 200 and the mandrel 100 when the ring 200 is received within the central cavity 110 of the mandrel 100 as depicted in FIG. 3. In an exemplary embodiment, the ring 200 may preferably comprise a polymer material and may be thin enough to be deformed and fit within a perimeter 122 of the central cavity 110. Of course, other methods of retaining the ring 200 within the mandrel 100 may be employed.

FIG. 3 shows a mandrel/optic disc assembly 10 according to one embodiment including the mandrel 100 according to FIG. 1 and the ring 200 according to FIG. 2 holding a lens blank 204 onto the mandrel 100. The ring 200 is formed with a ledge portion 202 on its inner circumference. The ledge portion 202 is configured to hold a lens blank 204 onto the mandrel 100 by pressing down on a top surface, second surface 210, of the lens blank 204 while the bottom surface, first surface 208, of the lens blank 204 is supported by the plurality of projections 112 of the mandrel 100. As shown in FIG. 3, the central axis of the lens blank 204 is received concentrically with the central axis (X) of the mandrel 100 and is disposed over the hollow channel 116. The lens blank 204 is preferably configured to occupy at least a portion of space formed by the central cavity 110 and a portion of space formed by the second cavity 114.

In an exemplary embodiment, the ring 200 has a plurality of holes 212 formed along its inner periphery on an inner peripheral surface 201. In this embodiment, the plurality of holes 212 are formed along the portion of the inner peripheral surface 201 that forms the ledge portion 202. Preferably, the plurality of holes 212 are disposed symmetrically around the center of the ring 200. In this embodiment, eight holes 212 are formed at approximately 45 degree intervals along the inner periphery of the ring 200 along the ledge portion 202. In one exemplary embodiment, the diameter of each of the plurality of holes 212 is approximately 0.75 mm.

As discussed further below, the plurality of holes 212 form channels through which a liquid, preferably water, may be introduced into a space 405 formed below the first surface 208 of the lens blank 204 as the lens blank 204 is supported by the plurality of projections 112 of the mandrel 100 and held by the ring 200. For the manufacturing of hydrophobic lenses from the lens blank 204 according to an exemplary embodiment, water is introduced through the plurality of holes 212 into the space 405 formed between the first surface 208 and the mandrel 100. The water filled mandrel 100 is then cooled so that the water freezes to ice. The resulting ice provides stability to the lens blank 204 as the lens blanked 204 is milled.

A method of using the mandrel 100 for manufacturing a lens, such as an intraocular lens will now be described.

Figure 4A:
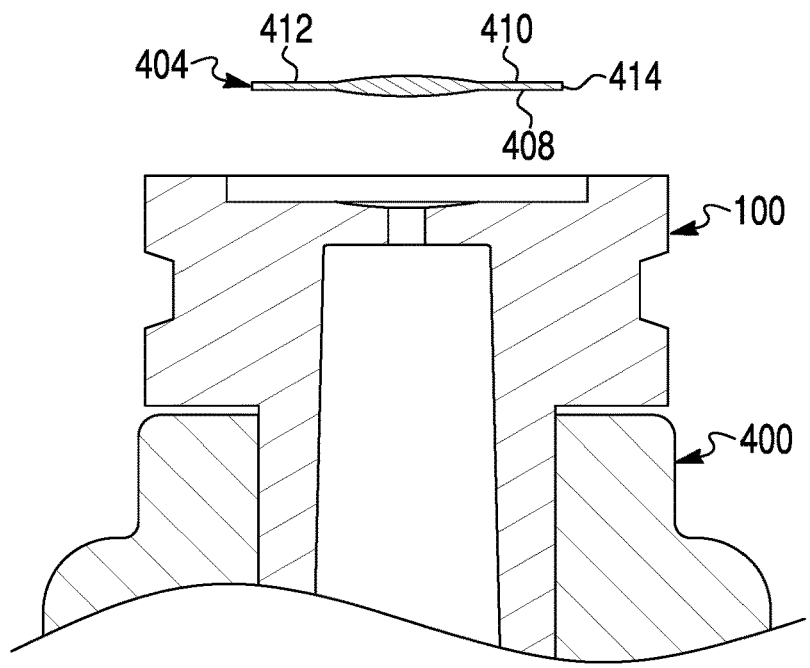
FIG. 4A shows a cross-sectional view of a lens blank being placed on a mandrel according to one embodiment.

As shown in FIG. 4A, a mandrel 100 according to one embodiment is placed in an ultra-precision collet 400. In this exemplary embodiment, a lens blank 204, for example, a hydrophobic optic disc 404, is placed precisely on the central axis (X) of the mandrel 100. The hydrophobic optic disc 404 described herein may be configured as described above with regard to the lens blank 204. Placement of the hydrophobic optic disc 404 may be performed using an optical centering device, such as that described in commonly assigned U.S. Pat. No. 8,854,611, the entire contents of which are hereby incorporated by reference.

Figure 4B:
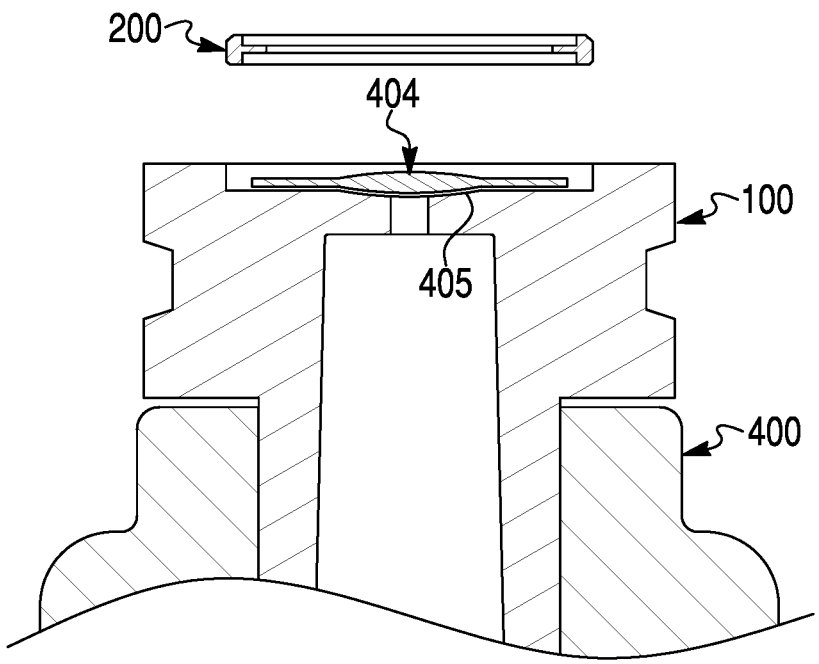
FIG. 4B shows a cross-sectional view of a ring being positioned onto a mandrel to hold a lens blank/optic disc according to one embodiment.
Figure 4C:
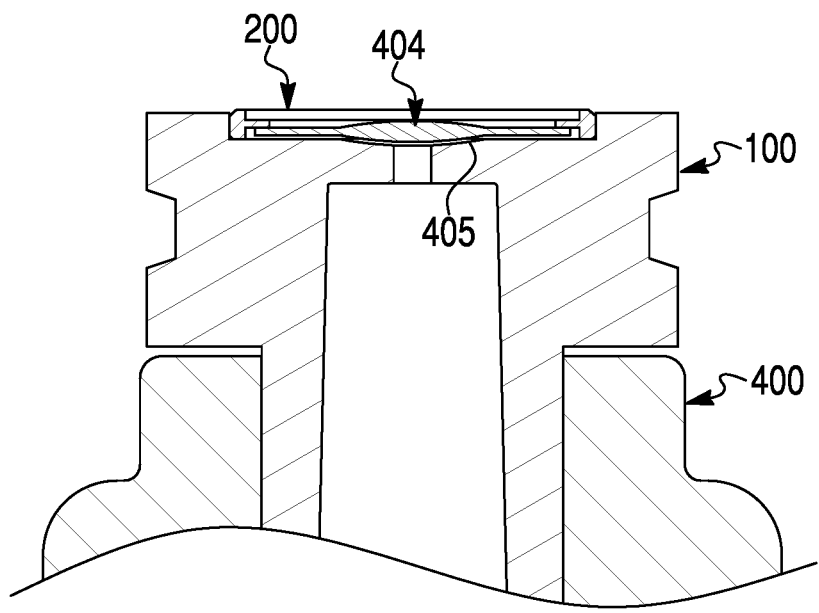
FIG. 4C shows a cross-sectional view of a mandrel/optic disc assembly positioned within a collet according to one embodiment.

As shown in FIGS. 4B and 4C, a compression ring 200 is then applied over the top surface 410 of the optic disc 404, so as to hold the optic disc 404 in its precise location on the mandrel 100. The bottom surface 408 of the optic disc 404 is supported on the mandrel 100 by the plurality of projections 112 formed on the bottom surface 120 of the central cavity 110 of the mandrel 100 to create a space 405. In an exemplary embodiment, the space 405 is formed below the flat portion 412 of the optic disc 404 that will be milled to become the haptic of the intraocular lens and the top surface of the lens blank holding section 105 of the mandrel 100. In one exemplary embodiment, the space 405 has a height of 0.250 mm.

The top surface 410 of the optic disc 404 may now be milled to form a lens such as an intraocular lens. One advantage provided by the embodiments described herein is that the mandrel/optic disc assembly comprising the mandrel 100 and the optic disc 404 (held precisely with the compression ring 200) can be packaged and shipped to other locations for completion of manufacturing to form lenses having desired optical characteristics. Additionally, because the mandrel/optic disc assembly is shelf-stable, it can be held in inventory for prolonged periods of time before completion of manufacturing.

Figure 5A:
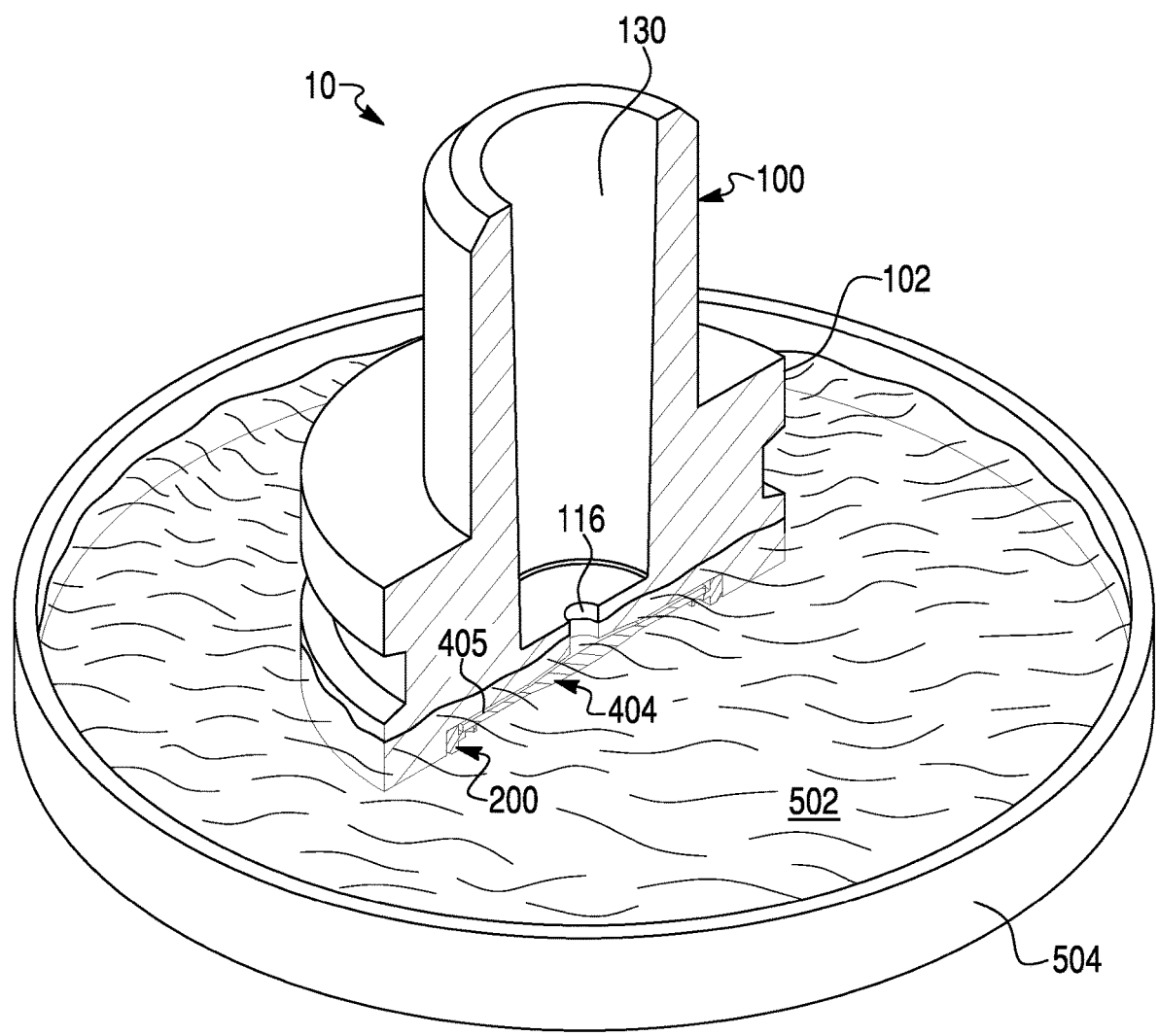
FIG. 5A shows a cross-sectional view of a mandrel/optic disc assembly according to one embodiment being inverted into a container of water so as to allow a space between the optic disc and the mandrel to be filled with water.
Figure 5B:
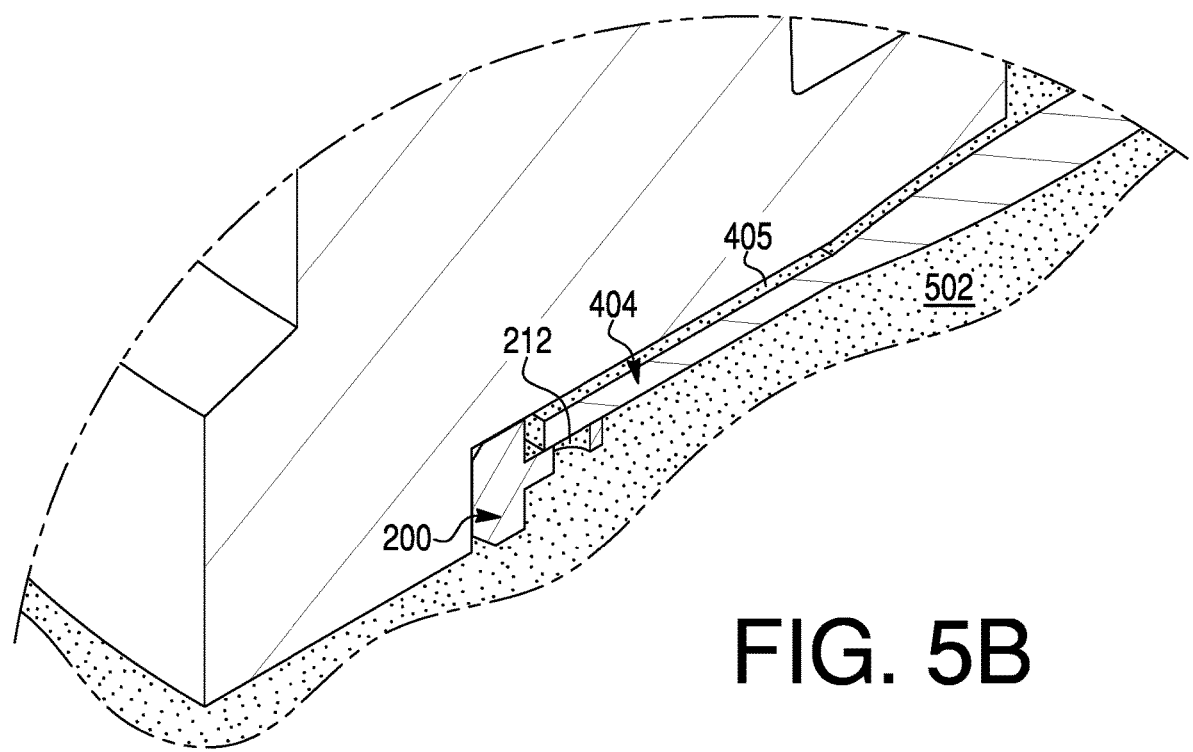
FIG. 5B is an enlarged view of a portion of the mandrel/optic disc assembly according to FIG. 5A in which water fills the space between the optic disc and the mandrel.

At a desired time for manufacturing, the space 405 between the optic disc 404 and the surface of the lens blank holding section 105, including the central cavity 110, of the mandrel 100 is filled with a suitable liquid, preferably water 502. For example, as illustrated in the embodiment depicted FIGS. 5A and 5B, the mandrel/optic disc assembly may be inverted and the space 405 filled by submerging at least a portion of the head portion 102 of the mandrel 100 (in which the optic disc 404 is held) in a container 504 configured to hold water 502. In this embodiment, water 502 may flow through the plurality of holes 212 in the ring 200 into the space 405 between a surface of the mandrel 100 and the optic disc 404. The central channel 116 provides an outlet for air forced out of the space 405 as water 502 fills the space 405. The hollow center channel 116 may be configured to communicate with an internal volume 130. The filled mandrel/optic disc assembly may then be placed into a precision collet 400, for example a milling collet 600, for further processing. In this embodiment, water 502 is retained in the space 405 by surface tension as the mandrel 100 is removed from the container 504.

Figure 6A:
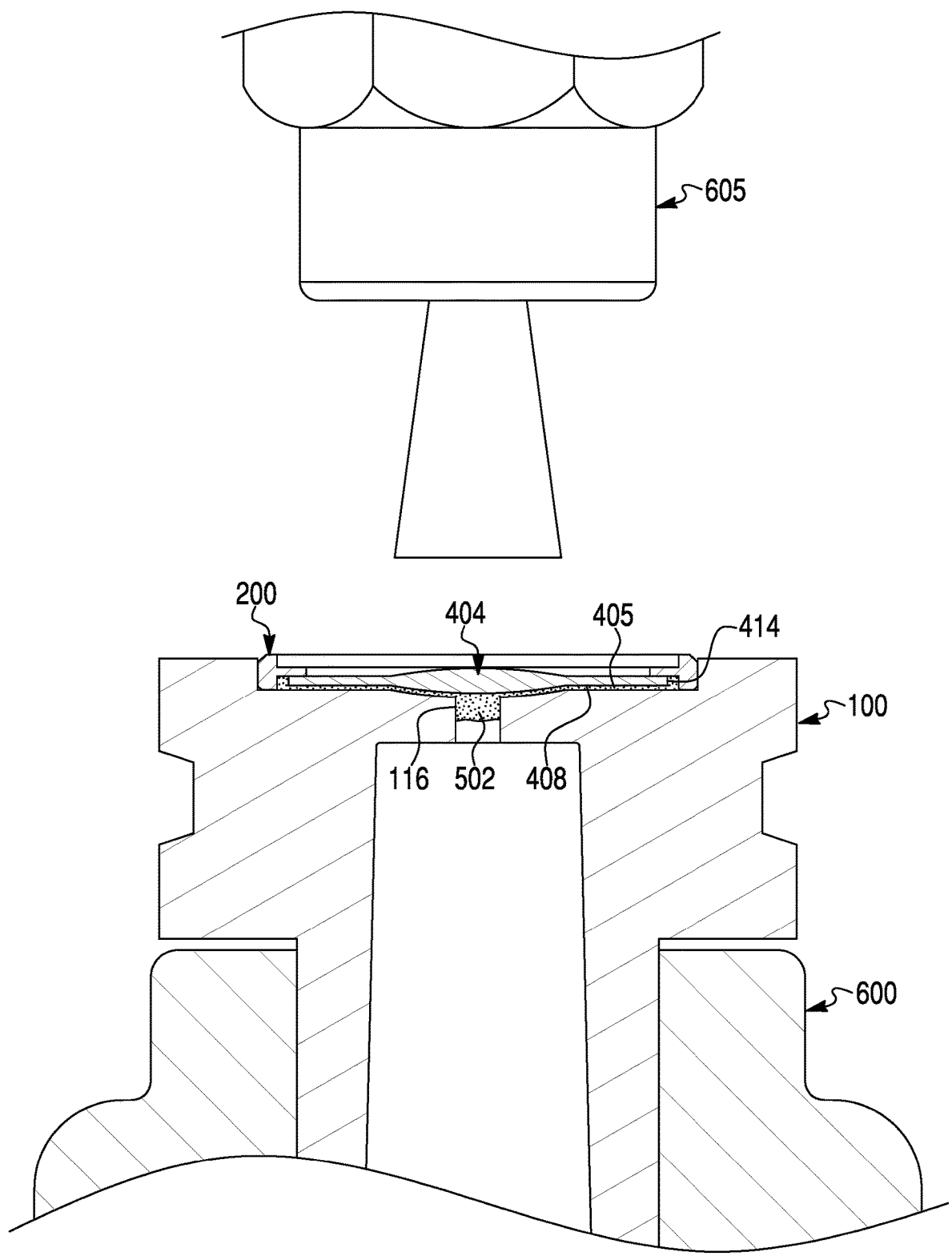
FIG. 6A shows a cross-sectional view of a mandrel/optic disc assembly positioned within a collet being cooled according to one embodiment.

As shown in FIG. 6A, the liquid filled mandrel/optic disc assembly according to one embodiment is then cooled in order to freeze the liquid 502 in the space 405 between the optic disc 404 and the mandrel 100. In this exemplary embodiment, the liquid filled mandrel 100 may be placed in a milling collet 600 and cooled with a cooling apparatus 605 configured to blow cold air over the mandrel/optic disc assembly in order to freeze the liquid 502 contained within the mandrel/optic disc assembly. In an alternative embodiment, the mandrel/optic disc assembly may be placed in a freezer.

Figure 6B:
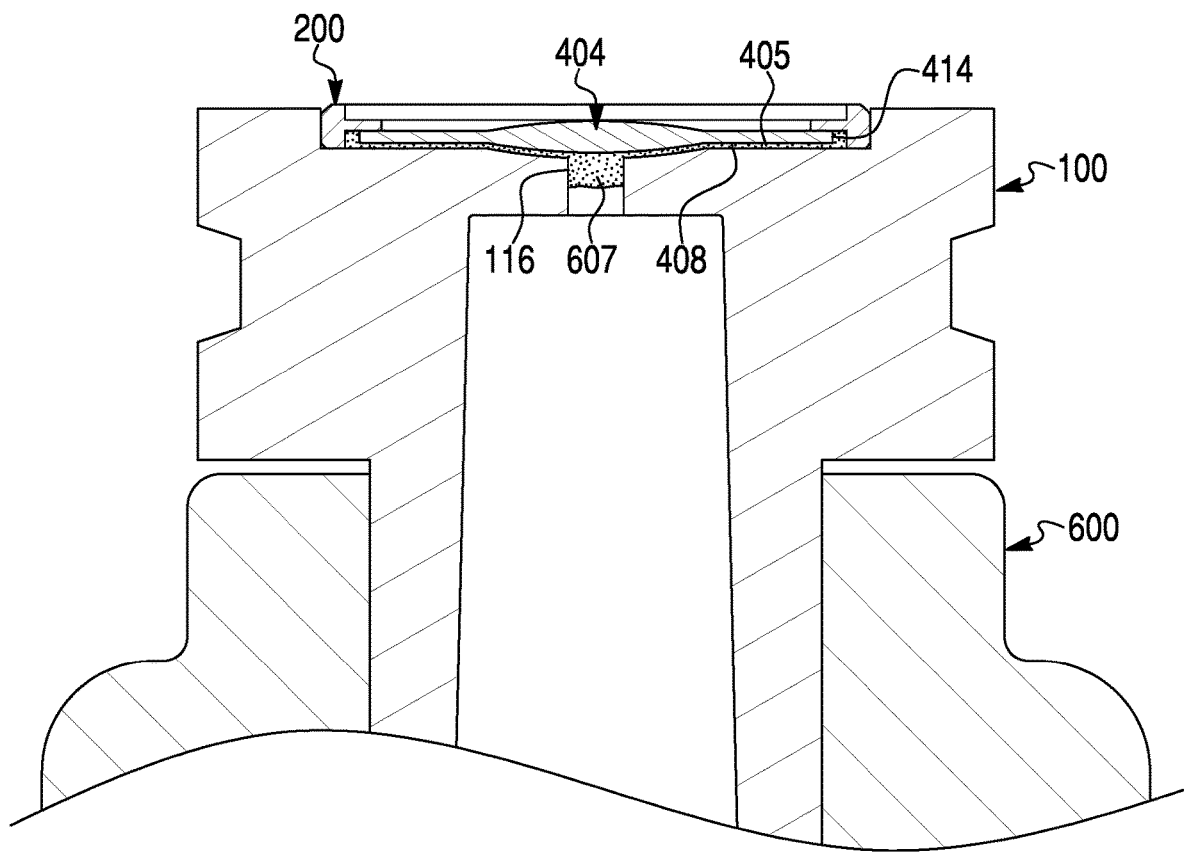
FIG. 6B shows a cross-sectional view of a mandrel/optic disc assembly positioned within a collet in which ice a frozen liquid is formed within a space between the optic disc and the mandrel so as to support the optic disc according to one embodiment.

The liquid 502 is frozen to form a solid surface (e.g., ice 607) within the mandrel/optic disc assembly as illustrated in FIG. 6B. As the water 502 freezes and expands, it may flow through the plurality of holes 212 in the ring 200 and/or into the center channel 116 of the mandrel 100. In this embodiment, the ice 607 surrounds at least the bottom surface 408 of the optic disc 404 and side surfaces 414 of the optic disc 404, thereby holding the optic disc 404 firmly in place. The ice 607 provides enhanced stability for the optic disc 404 during milling.

Figure 6D:
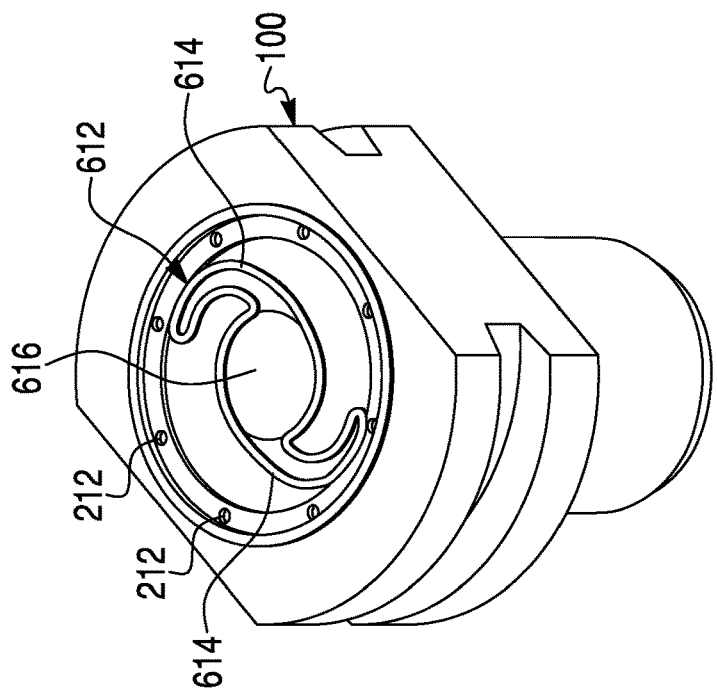
FIG. 6D shows a milled optic disc within a mandrel assembly according to one embodiment.
Figure 6C:
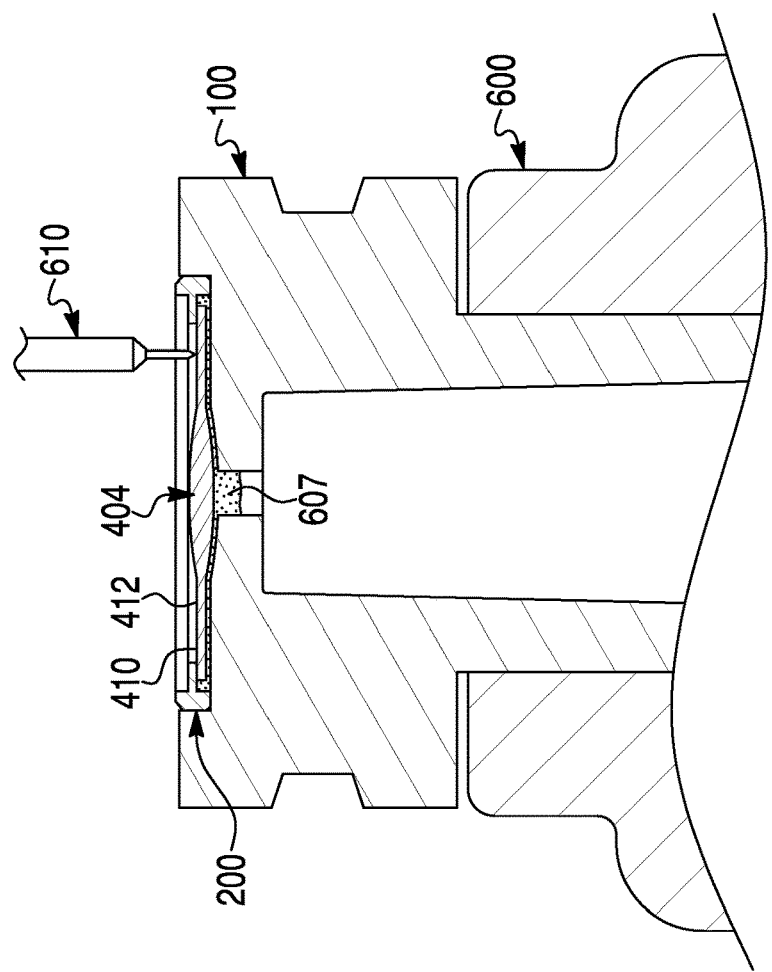
FIG. 6C shows a perspective view of a milling operation of an optic disc as it is positioned on a mandrel assembly positioned within a collet according to one embodiment.

As illustrated in the exemplary embodiment depicting a method of using the mandrel 100 for the manufacturing of a lens shown in FIGS. 6C and 6D, the top (second) surface 410 of the optic disc 404 is milled with a precision mill 610, such as a diamond end mill, to form haptic portions 614 and to complete the lens 612 including haptic portions 614 and optic portion 616. Milling may include cutting through the optic disc 404 to form the haptic portions 614. Preferably, the mill 610 is configured to cut through the optic disc 404 and into the ice 607 at defined locations to avoid damaging the underlying plurality of projections 112 configured to support the optic disc 404. The ice 607 provides enhanced stability during milling. After milling, the water 502 is allowed to melt, and the finished lens 612 may be cleaned with more water, inspected, packaged and sterilized.

It will be appreciated by those of skill in the art that embodiments of the disclosed invention provides several advantages. For example, the mandrel 100 maintains the lens blank 204, or optic disc 404, in precise alignment to facilitate subsequent manufacturing of a lens 612. Further, the mandrel 100 permits a lens blank 204, or optic disc 404, to be positioned on the mandrel 100 such that the position of the lens blank 204, or optic disc 404, may be maintained over a prolonged period of time before the completion of a lens 612. Additionally, the lens blank holding section 105, including the central cavity 110 and second cavity 114 formed within the mandrel 100, may accommodate the formation of ice 607 to support the optic disc 404 during cryogenic milling.

Figure 7:
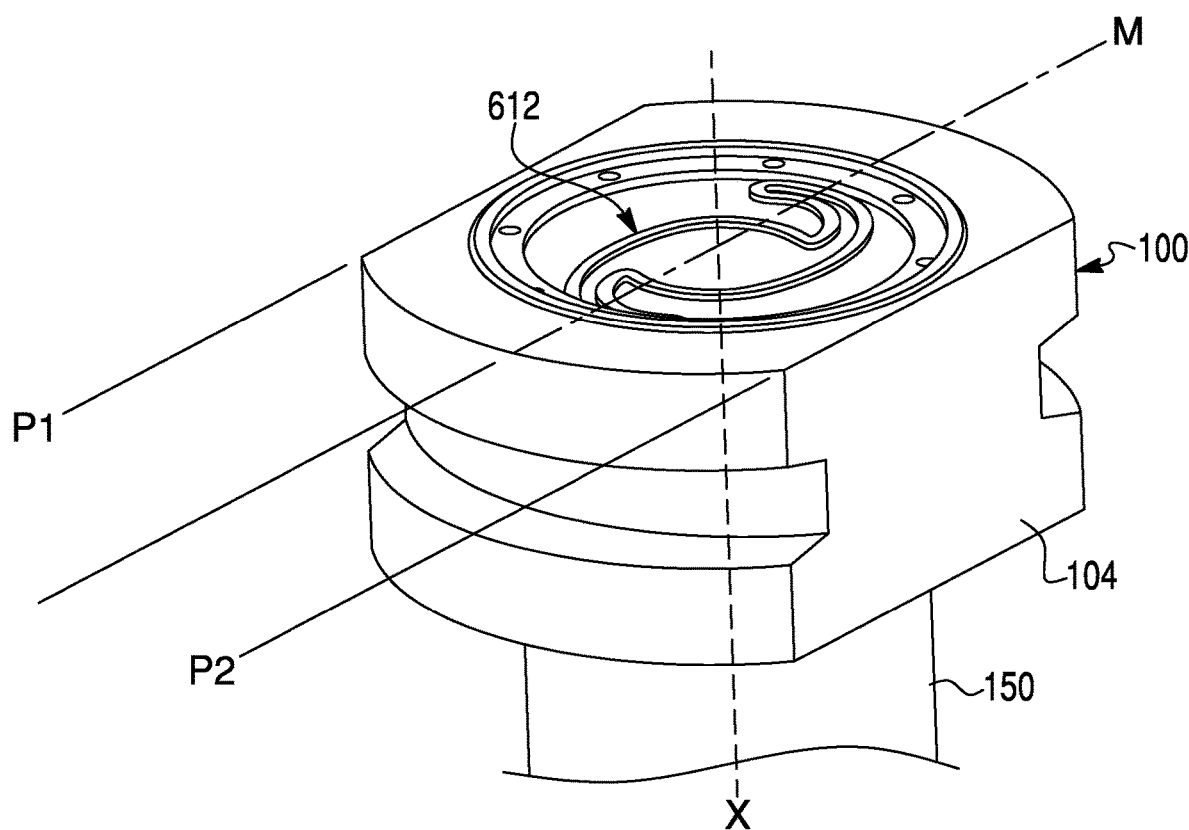
FIG. 7 shows a milled optic disc within a mandrel assembly according to one embodiment and the manner by which the haptic meridian may be aligned with the mandrel.

FIG. 7 is a perspective view illustrating a finished lens 612 formed from a lens blank 204, or optic disc 404, and held within a mandrel 100 by a ring 200 according to one embodiment. As shown in FIG. 7, the meridian of haptics (M) formed by milling the optic disc 404 runs through the center of the surface of the mandrel 100 at a central axis (X) of the mandrel 100 and is parallel to one or more substantially planar side surfaces 104 of the mandrel head 102. In an exemplary embodiment, the central axis (X) of the mandrel 100 may also include the central axis of the hollow mandrel shank 150 and/or the central axis of the lens blank 204, optic disc 404, or finished lens 612. In this embodiment, the mandrel 100 has two parallel, planar side surfaces 104 including parallel lines P1 and P2, respectively, as depicted in FIG. 7.

Figure 8:
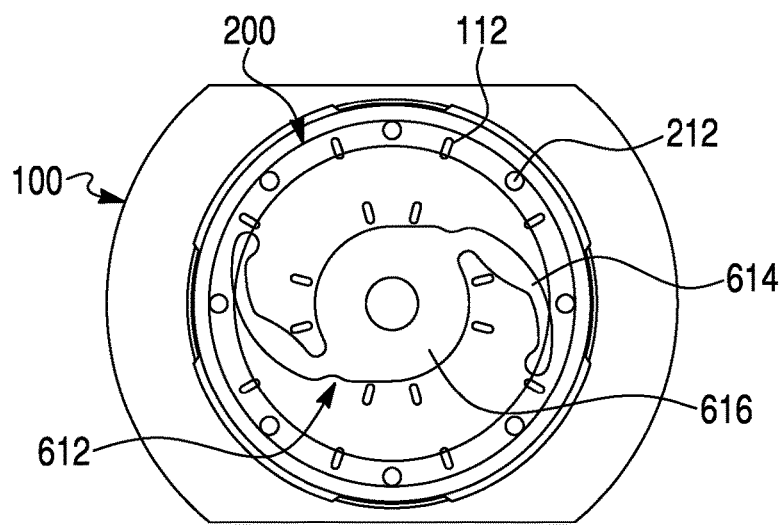
FIG. 8 shows a top view of an intraocular lens that is formed from an optic disc that is held by a mandrel assembly according to one embodiment.

FIG. 8 is a top plan view illustrating the relative position of a finished lens 612 formed from a lens blank 204, or optic disc 404, as it is held within the mandrel 100 according to one embodiment. As shown in this embodiment, the optic disc 404 is centered precisely on the mandrel 100 and retained by the ring 200. The plurality of projections 112 of the mandrel 100 are located outside of the portions of the finished lens 612 formed from the optic disc 404 that are milled or machined to form the intraocular lens 612. For example, the haptic portions 614 extend between the plurality of projections 112, which are disposed radially from the central axis (X) of the mandrel 100.

Figure 9:
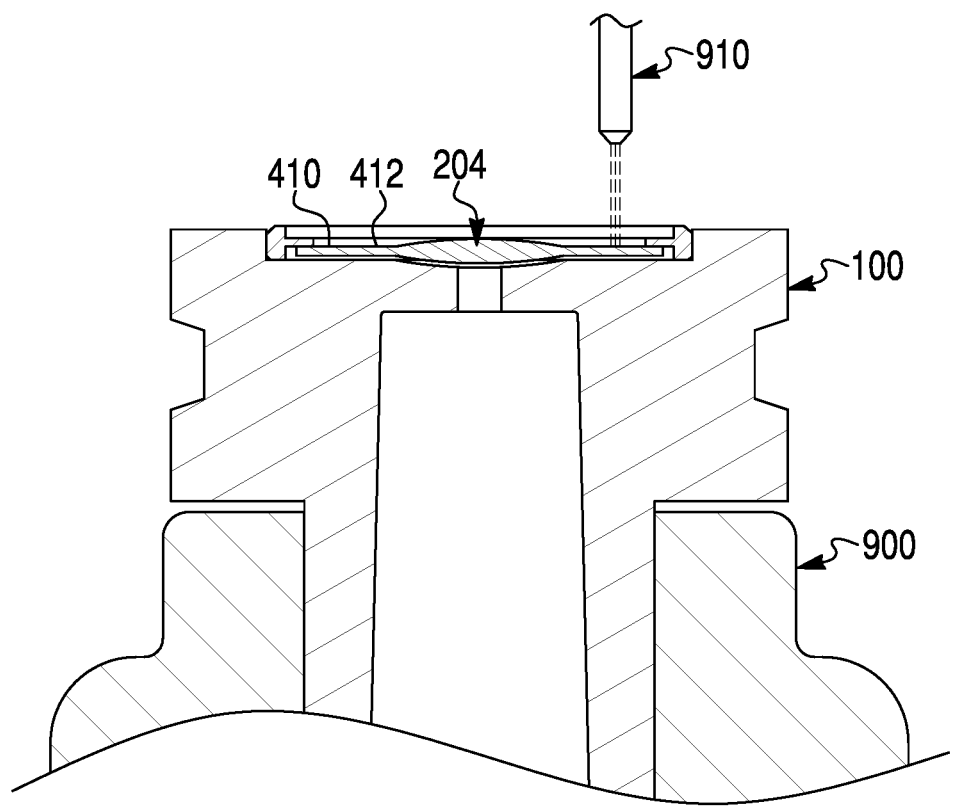
FIG. 9 shows a perspective view of a mandrel/optic disc assembly in which a lens is formed with a laser while the mandrel is held in a vacuum collet according to one embodiment.

While the mandrel 100 according to one embodiment may be used advantageously to cryogenically mill a lens 612, the invention is not limited to the above described embodiments and a lens 612 may be formed in other ways using the mandrel 100. As illustrated in the embodiment depicting a method of using the mandrel 100 for the manufacturing of a lens shown in FIG. 9, a mandrel/disc assembly according to some embodiments may be inserted into a vacuum collet 900. In this embodiment, a lens 612 may be manufactured with a laser 910.

In such an alternative process, it may not be necessary to introduce a liquid, such as water 502, into the mandrel 100. Accordingly, mandrels 100 according to this alternative embodiment may be used with lens blanks 204 formed of either a hydrophilic or a hydrophobic material. By affixing the lens blank 204 to the mandrel 100 with a ring 200 and supporting the lens blank 204 with a plurality of projections 112, the use of a blocking material, such as wax (i.e., for use with hydrophilic lens materials) or ice 607 (i.e., for use with hydrophobic lens materials) may not be necessary.

From the foregoing description, it will be understood that mandrels according to the invention may be used to hold a lens blank with precise alignment for later manufacturing. Mandrels according to certain embodiments of the invention are particularly useful in holding an optic disc in which the optic has been preformed, whereby haptics can be formed with precision and surface features milled to adjust optical characteristics. However, it will be understood that mandrels according to the invention can be used to position and hold universal lens blanks or other lens materials. Although specific features of the invention are shown in some drawings and not others, this is for convenience only as each feature may be combined with any or all of the other features in accordance with the invention. The words "including", "comprising", "having", and "with" as used herein are to be interpreted broadly and comprehensively and are not limited to any physical interconnection. Moreover, any embodiments disclosed in the subject of the application are not to be taken as the only possible embodiments.

The construction and arrangement of the apparatuses and methods as shown in the various exemplary embodiments are illustrative only. Although only a few embodiments have been described in detail in this disclosure, many modifications are possible (e.g. variations in sizes, dimensions, structures, shapes and proportions of the various elements, values of parameters, mounting arrangements, use of materials, colors, orientations, etc.). For example, the position of elements may be reversed or otherwise varied and the nature or number of discrete elements or positions may be altered or varied. Accordingly, all such modifications are intended to be included within the scope of the present disclosure. The order or sequence of any process or method steps may be varied or re-sequenced according to alternative embodiments. Other substitutions, modifications, changes, and omissions may be made in the design, operating conditions, and arrangement of the exemplary embodiments without departing from the scope of the patent disclosure.

In addition, any amendment presented during the prosecution of the patent application for this invention is not a disclaimer of any claim element presented in the application as filed: those skilled in the art cannot reasonably be expected to draft a claim that would literally encompass all possible equivalents, many equivalents will be unforeseeable at the time of the amendment and are beyond a fair interpretation of what is to be surrendered (if anything), the rationale underlying the amendment may bear no more than a tangential relation to many equivalents, and/or there are many other reasons the applicant cannot be expected to describe certain insubstantial substitutes for any claim element amended.

REFERENCE NUMERALS 10 mandrel/optic disc assembly
100 mandrel
102 top/head portion the mandrel
104 planar side surfaces of mandrel
105 lens blank holding section
110 central cavity
112 plurality of projections
114 second cavity
116 center channel
118 sidewall of central cavity
120 bottom surface of central cavity
122 perimeter of the central cavity
130 internal volume
150 mandrel shank
200 compression ring
201 inner peripheral surface
202 ledge portion of ring
204 lens blank
208 first surface of lens blank
210 second surface of lens blank
212 ring holes
218 sidewall of ring
400 collet
404 optic disc 405 space formed below lens blank to receive liquid
408 bottom surface of optic disc
410 top surface of optic disc
412 flat portion of optic disc
414 side surface of optic disc
502 water
504 container
600 milling collet
605 cooling apparatus
607 ice
610 precision mill
612 lens
614 haptic portions
616 optic portion
900 vacuum collet
910 laser
X central axis of mandrel
M meridian of haptics
P1 first parallel line
P2 second parallel line

What is claimed is:

1. A mandrel assembly for holding an intraocular lens blank, the mandrel assembly comprising:
a mandrel comprising:
a shank portion having a central axis, and
a lens blank holding section configured to hold a lens blank, the lens blank holding section including a central cavity formed concentrically with the central axis of the shank portion, the central cavity comprising a surface upon which projections are formed, and
a ring portion comprising an inner ledge, the mandrel assembly being configured such that, when said intraocular lens blank is held by said lens blank holding section and said ring portion is received within the central cavity, said projections contact and support a first bottom surface of the lens blank at a fixed distance from the surface of the central cavity and said inner ledge contacts and holds a second top surface of the lens blank opposing the first surface of the lens blank,
wherein the inner ledge of the ring portion is configured to hold the intraocular lens blank onto the mandrel by pressing down on the second top surface of the intraocular lens blank while the first bottom surface of the intraocular lens blank is supported by the plurality of projections of the mandrel,
wherein a space is formed between the first bottom surface of the lens blank and the surface of the central cavity as the lens blank is supported by the projections, and
wherein a hollow channel is formed within the central cavity, the hollow channel extending into the shank.

2. The mandrel assembly of claim 1, wherein the shank portion is configured to be received within a supporting collet.

3. The mandrel assembly of claim 1, wherein the mandrel further comprises a second cavity that is concentric with the central cavity and has a smaller cross-sectional diameter than the central cavity.

4. The mandrel assembly of claim 1, wherein the ring portion is configured to be held within the lens blank holding section by an interference fit formed with a sidewall portion of the central cavity.

5. The mandrel assembly of claim 1, wherein the ring portion further includes a plurality of holes formed along an inner peripheral surface thereof, the holes being configured to permit a liquid to be transferred into the space formed between the first surface of the lens blank as the lens blank is supported by the projections and the surface of the central cavity.

6. A method of making an intraocular lens, the method comprising:
providing a mandrel, the mandrel comprising:
a shank portion having a central axis, and
a lens blank holding section including a central cavity formed concentrically with the central axis of the shank portion, the central cavity comprising a surface upon which projections are formed;
positioning an intraocular lens blank in the central cavity of the mandrel;
providing a ring portion comprising an inner ledge;
fitting the ring portion to the mandrel such that the lens blank is held on the mandrel by said inner ledge contacting and holding a second surface of the lens blank and by said projections supporting a first surface of the lens blank at a fixed distance from the surface of the central cavity;
applying a liquid to a space formed between the first surface of the lens blank as the lens blank is supported by the projections and the surface of the central cavity;
freezing the liquid so that it supports the lens blank; and
forming a lens from the lens blank.

7. The method of claim 6, wherein an optical center of the lens blank is positioned concentrically with the central axis of the mandrel shank.

8. The method of claim 6, wherein the liquid comprises water.

9. The method of claim 6, wherein forming the lens comprises milling and/or machining the second surface of the lens blank as it is supported within the mandrel.

10. The method of claim 6, wherein the lens blank comprises a hydrophobic material.

11. The method of claim 6, wherein forming the lens includes forming haptic portions of an intraocular lens.

12. The method of claim 6, wherein the ring portion further includes a plurality of holes formed along an inner peripheral surface thereof, the holes being configured to permit a liquid to be transferred into the space formed between the first surface of the lens blank as the lens blank is supported by the projections and the surface of the central cavity.

* * * * *